United States Patent

Mariella, Jr.

[11] Patent Number: 6,154,276
[45] Date of Patent: Nov. 28, 2000

[54] WAVEGUIDE DETECTION OF RIGHT-ANGLE-SCATTERED LIGHT IN FLOW CYTOMETRY

[75] Inventor: Raymond P. Mariella, Jr., Danville, Calif.

[73] Assignee: The Regents of the University of California, Oakland, Calif.

[21] Appl. No.: 09/027,764

[22] Filed: Feb. 23, 1998

[51] Int. Cl.[7] ................................................. G01N 21/00
[52] U.S. Cl. ........................................... 356/337; 356/338
[58] Field of Search ..................................... 356/336, 337, 356/335, 410, 246, 440

[56] References Cited

U.S. PATENT DOCUMENTS

| | | | |
|---|---|---|---|
| 2,549,574 | 4/1951 | Condiff | 356/246 |
| 4,477,186 | 10/1984 | Carlson | 356/410 |
| 4,545,677 | 10/1985 | Chupp | 356/72 |
| 4,565,448 | 1/1986 | Abbott et al. | 356/339 |
| 5,412,466 | 5/1995 | Ogino | 356/246 |
| 5,475,487 | 12/1995 | Mariella, Jr. et al. | 356/336 |
| 5,581,349 | 12/1996 | Halaka | 356/336 |
| 5,594,545 | 1/1997 | Saito et al. | 356/440 |

*Primary Examiner*—Frank G. Font
*Assistant Examiner*—Michael P Stafira
*Attorney, Agent, or Firm*—John P. Wooldridge; Alan H. Thompson

[57] ABSTRACT

A transparent flow cell is used as an index-guided optical waveguide. A detector for the flow cell but not the liquid stream detects the Right-Angle-Scattered (RAS) Light exiting from one end of the flow cell. The detector(s) could view the trapped RAS light from the flow cell either directly or through intermediate optical light guides. If the light exits one end of the flow cell, then the other end of the flow cell can be given a high-reflectivity coating to approximately double the amount of light collected. This system is more robust in its alignment than the traditional flow cytometry systems which use imaging optics, such as microscope objectives.

37 Claims, 4 Drawing Sheets

WAVEGUIDE DETECTION OF RIGHT-ANGLE-SCATTERED LIGHT IN FLOW CYTOMETRY

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to flow cytometry, and more specifically, it relates to flow-cytometric biological, medical and other assays.

2. Description of Related Art

In previous Flow Cytometers (FCM), the right-angle-scatter (RAS) light has been viewed perpendicularly to the liquid flow, typically using a high NA microscope objective lens or fiber optic. Some of the difficulties associated with this approach are the very limited depth of field of high numerical aperture (NA) lenses, typically only a few μm, and the necessity to align precisely the exact focal point of the lens with that of the excitation light source. In addition, an obscuration bar is typically needed to block the laser light that has been scattered from the flow stream surface. As is shown in FIG. 1, a NA 0.6 lens captures less than 14% of all solid angles. U.S. Pat. No. 5,475,487, incorporated herein by reference, discloses the use of the unconfined aqueous flow stream itself as an index-guided optical waveguide, which captures approximately 17% of the solid angles. This very modest increase is augmented by the fact that all of the scattered light is trapped; there is no "focal point" for this configuration. Alignment simply requires aligning the light source onto the flow stream; no obscuration bar is needed, and the liquid optical waveguide is then automatically "aligned." This approach provides robust, stable light collection.

For the collection of elastically-scattered light, another immense advantage occurs: The background of scattered light is extremely low when using the flow-stream waveguide (FSW), because the same physical properties which confine the desired light within the stream also keep random scattered light out. It has been found that this FSW configuration gives the elastically-scattered RAS signal a much higher signal-to-noise ratio than that of forward scattered light. While this is extremely effective as described, there are applications, such as cell or chromosome sorting through the use of electrostatic deflection plates, which require the formation of a free stream of droplets after the cells or chromosomes have passed through the laser(s). In these cases, the previously patented technique (FSW) will not work because the formation of drops destroys the optical waveguide between the laser-excitation zone and the detector. Similarly, there are applications in which the necessary liquid flow is so slow that instabilities in the stream would also disrupt the optical waveguide between the laser-excitation zone and the detector.

SUMMARY OF THE INVENTION

It is an object of the present invention to provide improved techniques for measuring the right-angle-scattered light in a flow cytometer.

The new idea is to use a transparent flow cell as an index-guided optical waveguide, similar in some respects to U.S. Pat. No. 5,475,487. A detector for the flow cell but not the liquid stream would then be used to detect the Right-Angle-Scattered (RAS) Light exiting from one end of the flow cell. As before, the detector(s) could view the trapped RAS light from the flow cell either directly or through intermediate optical light guides. If the light exits the end of the flow cell referred to as "bottom", then the top of the flow cell could be given a high-reflectivity coating to approximately double the amount of light collected. This system would be much more robust in its alignment than the traditional flow cytometry systems which use imaging optics, such as microscope objectives.

Flow cytometry is used world-wide for biological and medical diagnostics as well as general characterization of particles in liquid mediums. As a health-care instrument, the invention can be used for blood diagnostics and/or DNA characterization. This kind of flow cytometer, when used to study peripheral or other blood cells, has considerable commercial application in clinical diagnostics laboratories, counting red blood cells or white blood cells, or both. Flow sorting is used to prepare chromosome libraries to sort x versus y sperm and to select stem cell for blood bone marrow transplantation after radiation therapy.

DETAILED DESCRIPTION OF THE INVENTION

The invention passes the liquid stream of a flow cytometer through a flow cell which is transparent to both the excitation light and the scattered light, including elastically scattered light and/or inelastically scattered light, as appropriate. A transparent flow cell is used as an index-guided optical waveguide, similar in some respects to U.S. Pat. No. 5,475,487, except that the cell is fabricated from a transparent material whose index of refraction at the scattered wavelengths is larger than that of the liquid stream and the air, as well. I.e., for a (typical) aqueous stream with n=1.33, quartz or glass with n=1.4 could be employed. A detector for the flow cell but not the liquid stream would then be used to detect the RAS light exiting from one or both ends of the flow cell. As before, the detector(s) could view the trapped RAS light from the flow cell either directly or through intermediate optical light guides.

Figure 2:
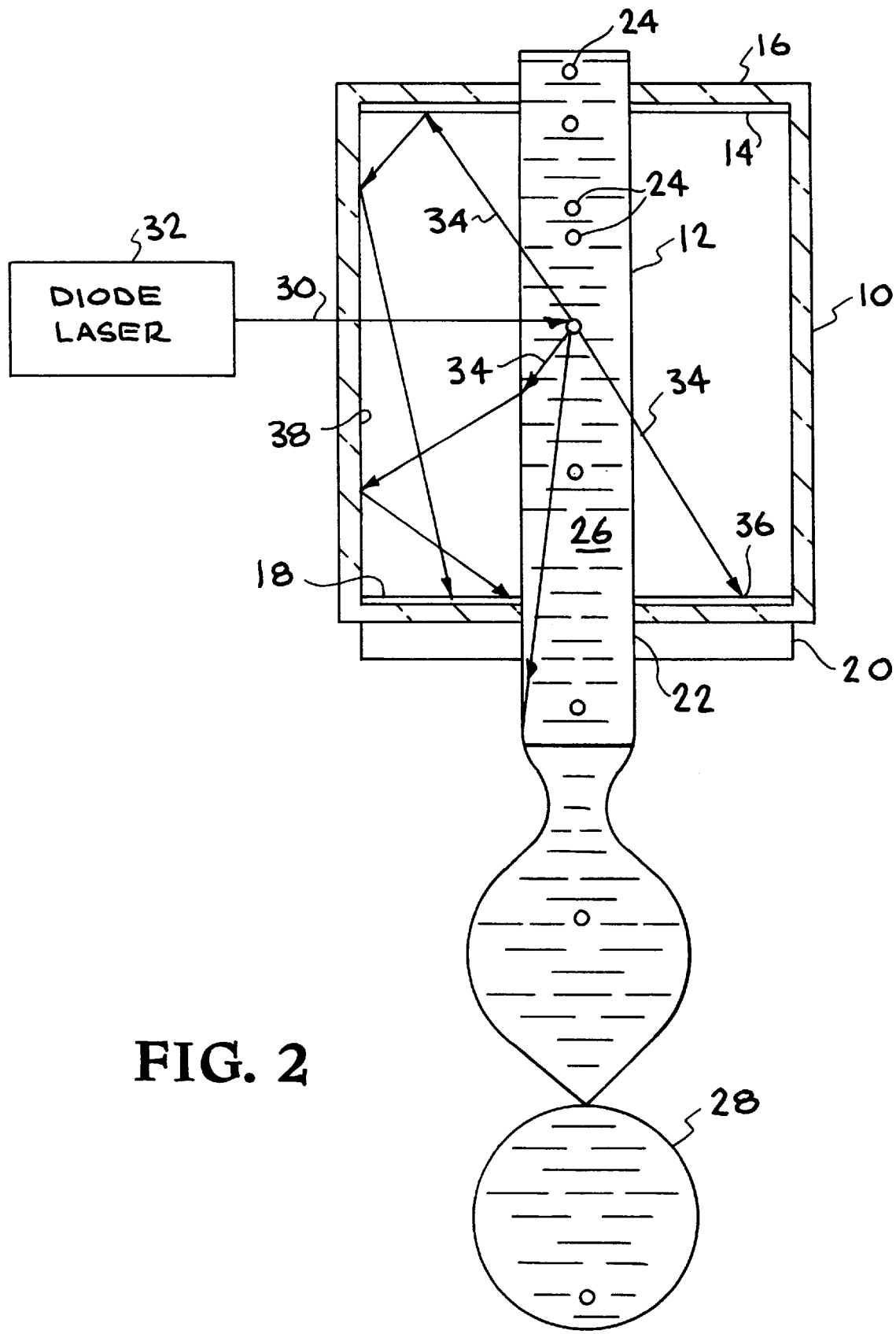
FIG. 2 shows a basic embodiment of the invention, which utilizes a transparent flow cell with a hollow flow capillary.

FIG. 2 shows a basic embodiment of the invention, which utilizes a transparent flow cell 10 with a hollow flow capillary 12. The transparent flow cell 10 may include a high-reflection coating 14 on one end 16, and may further include an anti-reflection coating on the other end 18. A detector 20 having a hole 22 is coupled to the end 18. In operation, cells, chromosomes, or other types of particulate 24 suspended in a liquid 26 flow through the hollow flow capillary 12 in the transparent flow cell 10, and through the hole 22 in detector 20 to form droplets 28. As the particulate 24 passes through the flow cell 10, a laser beam 30 from a laser 32 is directed through the transparent flow cell 10, where it interacts with the particulate 24 to produce, inter alia, scattered light 34. This scattered light 34 can propagate onto detector 20 in three ways: (i) by a direct path as e.g., at 36, (ii) by reflection from the high-reflection coating 14 on end 16 and subsequent waveguide transmission from the walls 38 of flow cell 10, or (iii) by waveguide transmission from the walls 38 of flow cell 10.

Any light trapped within the liquid stream is lost. Since the amount of confined light, roughly approximately equal to the area multiplied by the index of refraction, tends to be confined within the material with the higher index of refraction, and if the area of the flow cell (in the plane which is perpendicular to the flow direction) supports one or more index-guided waveguide modes, is much greater than the cross section of the flow stream, then very little light will be lost to the flow stream. Another advantage of this design is that the top end of the flow cell can be coated with a material that presents high reflectivity (HR) to the RAS which travels away from the etector. This HR material could either be metal or a broadband multilayer reflector, for example. The broadbanded nature of the detector is needed because the trapped RAS light, even if monochromatic, would strike the end at a variety of angles. Similarly, the exit face of the flow cell could be anti-reflection coated to increase the transmission of RAS light to the detector and, hence, the overall efficiency of the system.

Figure 1:
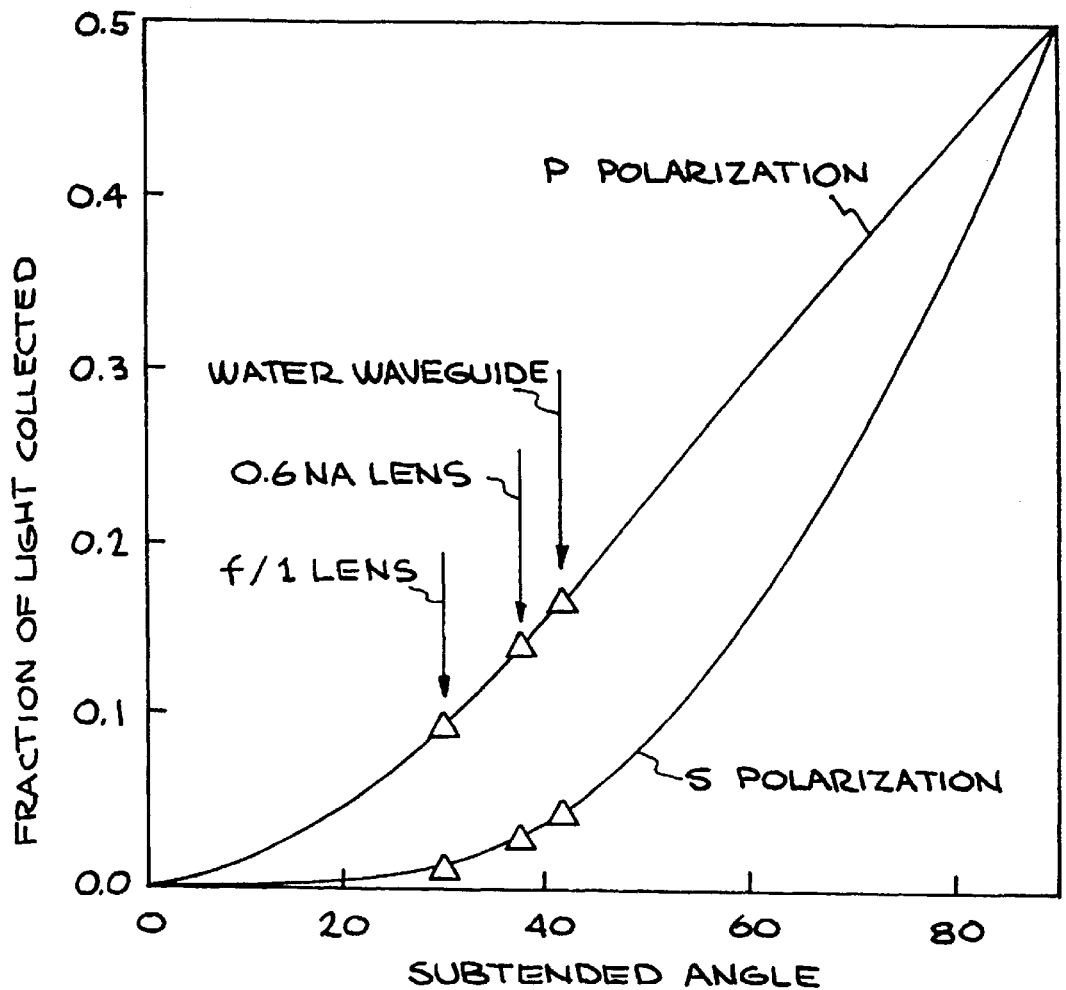
FIG. 1 shows that a lens having a numerical aperture of 0.6 captures less than 14% of all solid angles.
Figure 3:
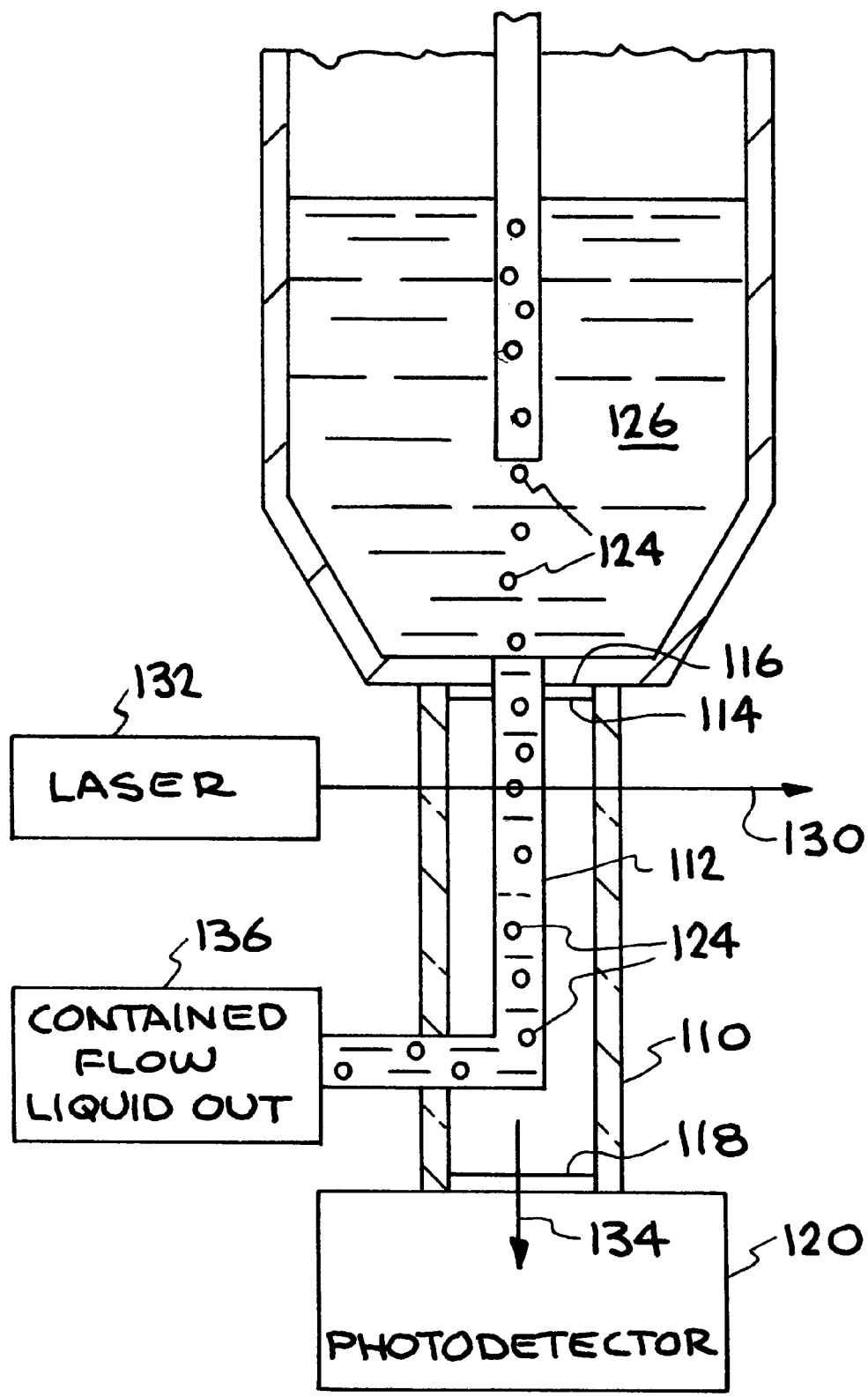
FIG. 3 shows an embodiment of the invention, where the transparent flow cell make a right angle such that fluid exits the flow cell at approximately a right angle, and light continues to travel straight.

FIG. 3 shows a second basic embodiment of the invention, which utilizes a transparent flow cell 110 with a hollow flow capillary 112. The transparent flow cell 110 make a right angle such that fluid exits the flow cell at approximately a right angle, and light continues to travel straight. The right angle bend in the liquid flow channel separates the liquid from the light guiding. The cell 110 may include a high-reflection coating 114 on one end 116, and may further include an anti-reflection coating on the other end 118. A detector 120 is coupled to the end 118. In operation, cells, chromosomes, or other types of particulate 124 suspended in a liquid 126 flow through the hollow flow capillary 112 in the transparent flow cell 110 to flow out of the system and into a containment system 136. As the particulate 124 passes through the flow cell 110, a laser beam 130 from a laser 132 is directed through the transparent flow cell 110, where it interacts with the particulate 124 to produce, inter alia, scattered light 134. Note that the orientation of the flow cell direction of flow is not relevant, which enables sorting or debubbling. This scattered light 134 can propagate onto detector 120 in the same three ways as described under FIG. 1. Additionally, some of the light trapped within the flow stream would be detected due to coupling from the hollow flow capillary 112. Some light is lost due to the blocking effect of the right angle made by the flow capillary as it exits the flow cell.

Figure 4:
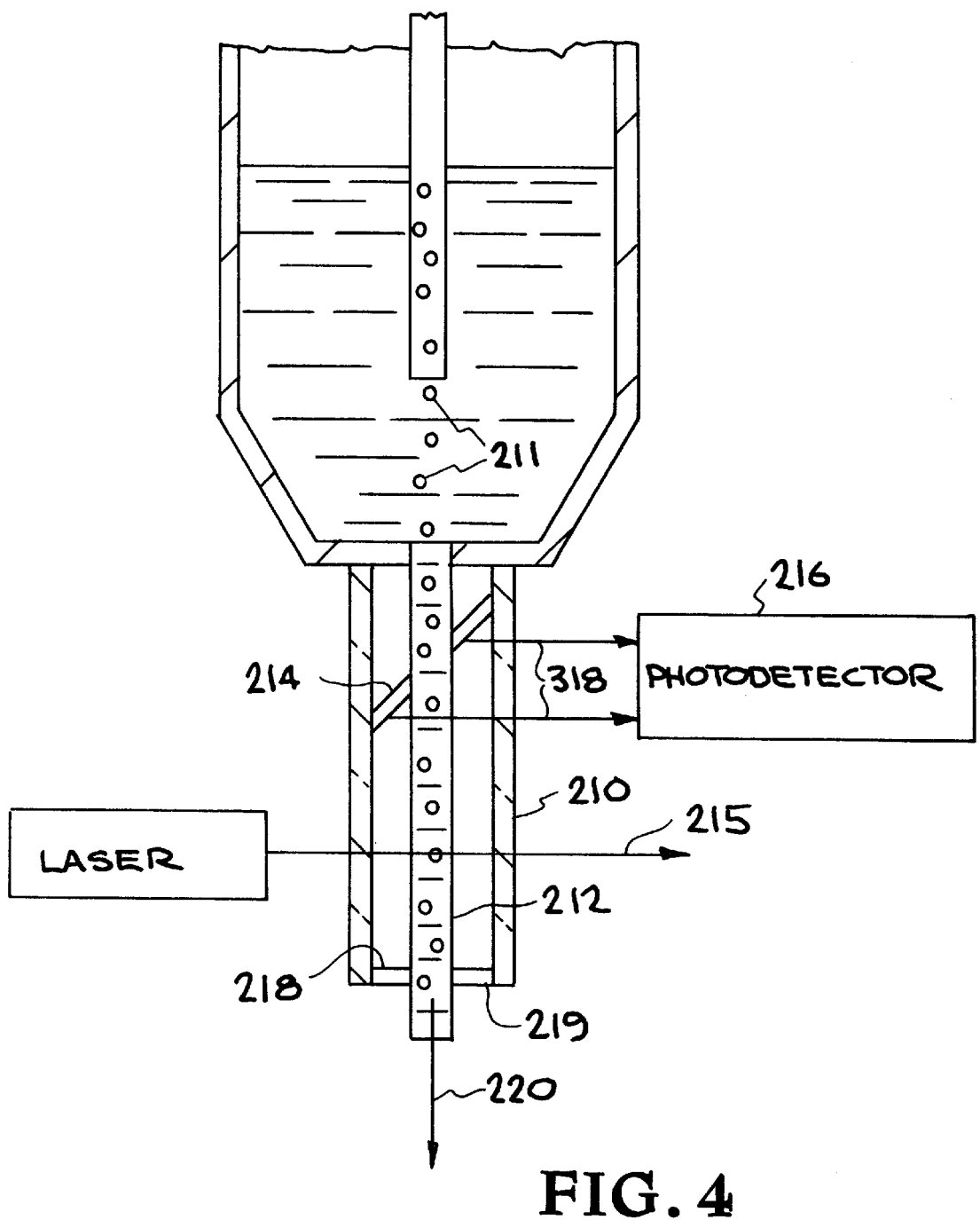
FIG. 4 shows another embodiment of the invention, where a reflecting surface, embedded within the flow cell in the liquid flow channel guides the induced scatter onto a photodetector.

FIG. 4 shows a third embodiment of the invention, which utilizes a transparent flow cell 210 with a hollow flow capillary 212. This embodiment includes a reflecting surface 214, embedded within the flow cell 210 in the liquid flow channel to guide the induced scatter onto a photodetector 216. As cells 211 flow by, they generate scatter in the laser beam 215. A portion 218 of this scatter reflects toward the high-reflective surface 214, and some of this light reflects from high-reflective surface to exit the system onto a photodetector 216. This embodiment may also include a high reflecting surface 218 at the exit of the flow cell. All of the light trapped within the flow stream would be lost. Fluid 220 containing particulate or cells 211 passes out of the system at the bottom 219 of the transparent flow cell 210.

Changes and modifications in the specifically described embodiments can be carried out without departing from the scope of the invention, which is intended to be limited by the scope of the appended claims.

The invention claimed is:

1. A flow cytometer flow cell, comprising:
   a transparent flow cell having a hollow flow capillary to allow the flow of a sheath liquid therethrough, wherein said transparent flow cell comprises a solid-state material having an index of refraction that is greater than that of said sheath liquid, wherein particles suspended in said sheath liquid will produce scattered light from a laser beam directed at said particles, wherein a first portion of said scattered light will propagate into said solid-state material of said transparent flow cell; and
   a detector positioned to detect a second portion of said first portion of said scattered light.

2. The flow cytometer flow cell of claim 1, wherein said detector further comprises a hole, wherein said detector is coupled to an end of said flow cell.

3. The flow cytometer flow cell of claim 1, further comprising a laser to provide a laser beam to be directed at said particles suspended in said sheath liquid.

4. The flow cytometer flow cell of claim 3, wherein said laser comprises a diode laser.

5. The flow cytometer flow cell of claim 2, wherein said transparent flow cell further comprises a high-reflection coating on the opposite end from said detector.

6. The flow cytometer flow cell of claim 2, wherein said transparent flow cell further comprises an anti-reflection coating on the same end as said detector.

7. The flow cytometer flow cell of claim 1, further comprising means for providing a liquid for input into said hollow flow capillary for production of said liquid sheath.

8. The flow cytometer flow cell of claim 1, wherein said transparent flow cell further comprises a cylindrical shape with a first end and a second end with a cylinder portion therebetween, wherein said cylinder portion comprises high-reflector material thereover except for a hole or absence of said high-reflector material thereon to allow passage of a laser beam into said transparent flow cell.

9. The flow cytometer flow cell of claim 8, wherein said first end comprises a high-reflection coating.

10. The flow cytometer flow cell of claim 8, wherein said second end comprises an anti-reflection coating, wherein said detector is coupled to said second end and said anti-reflection coating.

11. The flow cytometer flow cell of claim 2, wherein said hollow flow capillary exits said transparent flow cell at a location other than at the interface between said transparent flow cell and said detector.

12. The flow cytometer flow cell of claim 1, wherein a length of said hollow flow capillary is formed along the longitudinal axis of said transparent flow cell, wherein a second length of said hollow flow capillary is formed from an end of said first length toward the outer wall of and forming an opening in said flow cell, wherein said liquid sheath can move through said flow cell within said hollow flow capillary along said longitudinal axis and exit out of the side of said transparent flow cell.

13. The flow cytometer flow cell of claim 12, wherein said detector is coupled to an end of said flow cell.

14. The flow cytometer flow cell of claim 12, further comprising a laser to provide a laser beam to be directed at said particles suspended in said sheath liquid.

15. The flow cytometer flow cell of claim 14, wherein said laser comprises a diode laser.

16. The flow cytometer flow cell of claim 12, wherein said transparent flow cell further comprises a high-reflection coating on the opposite end from said detector.

17. The flow cytometer flow cell of claim 12, wherein said transparent flow cell further comprises an anti-reflection coating on the same end as said detector.

18. The flow cytometer flow cell of claim 11, further comprising means for providing a liquid for input into said hollow flow capillary for production of said liquid sheath.

19. The flow cytometer flow cell of claim 11, wherein said transparent flow cell further comprises a cylindrical shape with a first end and a second end with a wrapped plane portion therebetween, wherein said wrapped plane portion comprises high-reflector material thereover except for a hole or absence of said high-reflector material thereon to allow passage of a laser beam into said transparent flow cell.

20. The flow cytometer flow cell of claim 19, wherein said first end comprises a high-reflection coating.

21. The flow cytometer flow cell of claim 19, wherein said second end comprises an anti-reflection coating, wherein said detector is coupled to said second end and said anti-reflection coating.

22. The flow cytometer flow cell of claim 1, further comprising a high reflector surface embedded within said transparent flow cell, said high reflector surface having a hole to allow the flow of said sheath liquid through said hollow flow capillary, wherein said high reflector surface is configured to reflect said second portion of scattered light out of said transparent flow cell and onto said detector.

23. The flow cytometer flow cell of claim 22, wherein said detector is coupled to said flow cell where said second portion of said scattered light exits said transparent flow cell.

24. The flow cytometer flow cell of claim 22, further comprising a laser to provide a laser beam to be directed at said particles suspended in said sheath liquid.

25. The flow cytometer flow cell of claim 24, wherein said laser comprises a diode laser.

26. The flow cytometer flow cell of claim 22, wherein said transparent flow cell further comprises a high-reflection coating on a first end.

27. The flow cytometer flow cell of claim 22, wherein said transparent flow cell further comprises a high-reflection coating on a second end.

28. The flow cytometer flow cell of claim 22, further comprising means for providing a liquid for input into said hollow flow capillary for production of said liquid sheath.

29. The flow cytometer flow cell of claim 22, further comprising an anti-reflection coating on the surface of said transparent flow cell where light exits said transparent flow cell.

30. The flow cytometer flow cell of claim 22, wherein said transparent flow cell further comprises a cylindrical shape with a first end and a second end with a wrapped plane portion therebetween, wherein said wrapped plane portion comprises high-reflector material thereover except for a first hole or absence of said high-reflector material thereon to allow passage of a laser beam into said transparent flow cell and a second hole or absence of said high-reflector material thereon to allow passage of a laser beam out of said transparent flow cell.

31. The flow cytometer flow cell of claim 30, wherein said first end comprises a high-reflection coating.

32. The flow cytometer flow cell of claim 30, wherein said second end comprises a high-reflection coating.

33. The flow cytometer flow cell of claim 30, further comprising an anti-reflection coating on the surface of said transparent flow cell where light exits said transparent flow cell.

34. The flow cytometer flow cell of claim 1, further comprising means for sorting cells that exit said hollow flow capillary.

35. The flow cytometer flow cell of claim 12, further comprising means for sorting cells that exit said hollow flow capillary.

36. The flow cytometer flow cell of claim 22, further comprising means for sorting cells that exit said hollow flow capillary.

37. The flow cytometer flow cell of claim 1, further comprising an extended light source to provide light to be directed at said particles suspended in said sheath liquid.

* * * * *